US007718360B2

(12) United States Patent
Chakrabarti et al.

(10) Patent No.: US 7,718,360 B2
(45) Date of Patent: May 18, 2010

(54) COMPOSITION (RCUD) FOR PROTECTING AND/OR REPAIRING DNA FROM OXIDATIVE DAMAGES AND A METHOD THEREOF

(75) Inventors: Tapan Chakrabarti, Nagpur (IN); Saravana Devi Sivanesan, Nagpur (IN); Krishnamurthi Kannan, Nagpur (IN); Dipanwita Dutta, Nagpur (IN); Rishi Narain Singh, Nagpur (IN); Sunil Balkrishna Mansinghka, Nagpur (IN); Suresh Haribhau Dawle, Nagpur (IN)

(73) Assignee: Council of Scientific & Industrial Research, New Dehli (IN)

( * ) Notice: Subject to any disclaimer, the term of this patent is extended or adjusted under 35 U.S.C. 154(b) by 0 days.

(21) Appl. No.: 10/404,448

(22) Filed: Apr. 2, 2003

(65) Prior Publication Data

US 2004/0198769 A1   Oct. 7, 2004

(51) Int. Cl.
*C12Q 1/68* (2006.01)
*A61K 35/22* (2006.01)

(52) U.S. Cl. .......................................... 435/6; 424/543

(58) Field of Classification Search ................ 424/545, 424/543; 435/6; 536/22.1; 436/172
See application file for complete search history.

(56) References Cited

U.S. PATENT DOCUMENTS

| | | | | |
|---|---|---|---|---|
| 5,736,576 | A | * | 4/1998 | Kun et al. .................... 514/570 |
| 6,060,310 | A | * | 5/2000 | Cho-Chung .................. 435/375 |
| 2002/0164378 | A1 | * | 11/2002 | Khanuja et al. ............. 424/545 |

OTHER PUBLICATIONS

Birnboim et al., "Fluorometric method for rapid detection of DNA strand breaks in human white blood cells produced by low doses of radiation," Cancer Res 41(5):1889-1892, 1981.*
Lin et al., "Scavenging of reactive oxygen species by a urinary preparation," Am J Chin Med 28(2):251-258, 2000.*
Nunoshiba et al., "Role of iron and superoxide for generation of hydroxyl radical, oxidative DNA lesions, and mutagenesis in *Escherichia coli*," J Biol Chem 274(49):34832-34837, 1999.*
Wahl et al., Simultaneous analysis of the di(2-ethylhexyl)phthalate metabolites 2-ethylhexanoic acid, 2-ethyl-3-hydroxyhexanoic acid and 2-ethyl-3-oxohexanoic acid in urine by gas chromatography-mass spectrometry, J Chromatogr B Biomed Sci Appl 758(2): 213-219, 2001.*
Wieczorek et al., "Determination of mixtures of urinary benzoic, 3- and 4-methylbenzoic, and mandelic acids by gas chromatography," Arch Toxicol 42(4):281-287, 1979.*

(Continued)

*Primary Examiner*—Karen Cochrane Carlson
*Assistant Examiner*—Rosanne Kosson
(74) *Attorney, Agent, or Firm*—Sughrue Mion, PLLC

(57) ABSTRACT

A composition useful for protecting and/or repairing DNA from oxidative damages said composition comprising redistilled cow's urine distillate (RCUD) having components benzoic acid, and hexanoic acid, with ammonia content of the composition ranging between 5-15 mg/L, and optionally along with anti-oxidants; and a method of protecting and/or repairing DNA from oxidative damages using composition of claim 1, said method comprising steps of estimating the amount of folded DNA in a sample, mixing the said composition to the said DNA either before or after the exposure of the DNA to the oxidatively DNA-damaging agent, and determining percentage folded DNA in the mixture showing protection and/or repair of DNA from oxidative damages.

10 Claims, 1 Drawing Sheet

OTHER PUBLICATIONS

Figure 1:
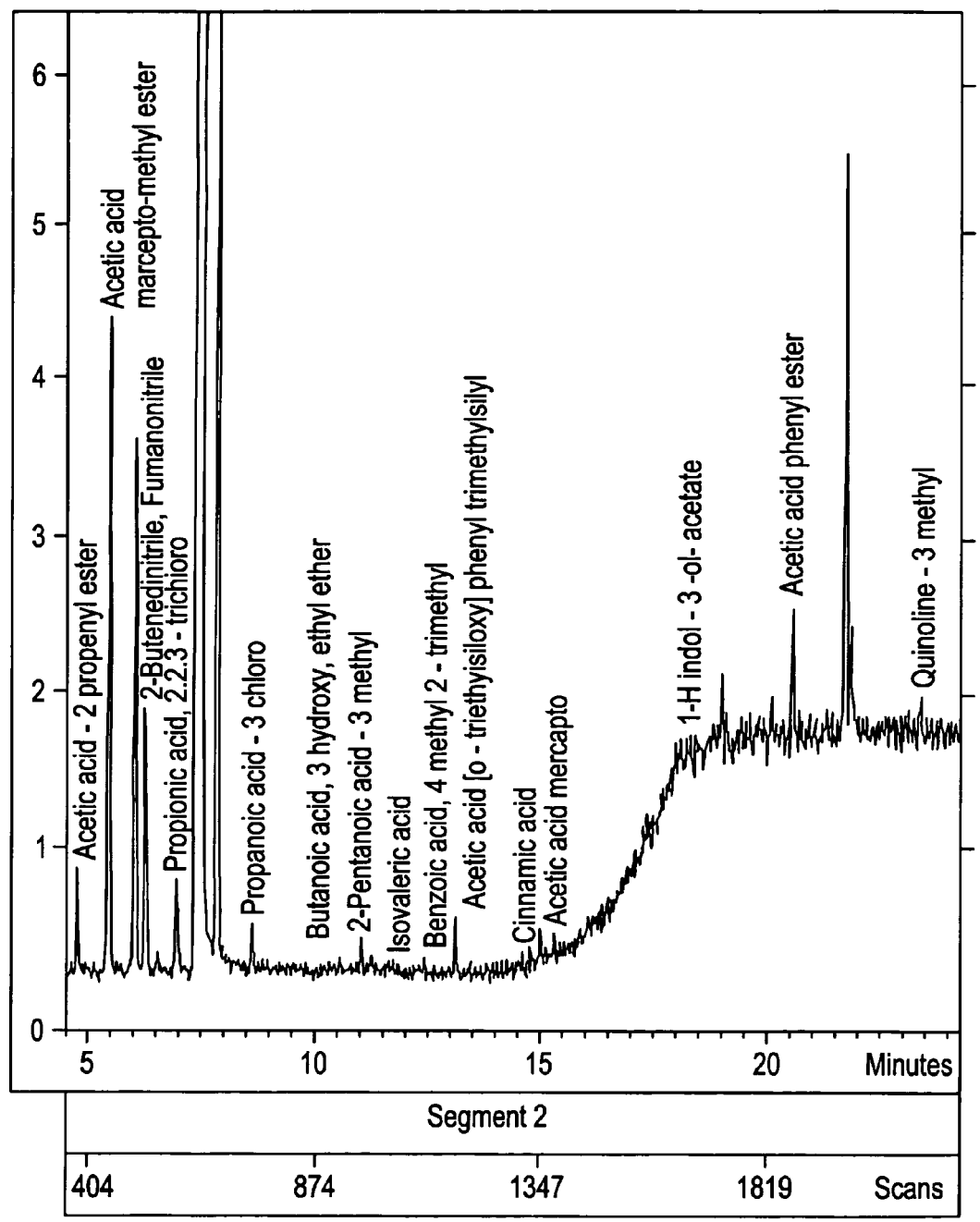

Stedman's Medical Dictionary, p. 1893, Williams & Wilkins, Baltimore, MD, 1995.*

Bergman, Molecular Structures: Actinomycin D, http://www.biologie.uni-hamburg.de/lehre/bza/actd/eactd.htm, printed on Jan. 4, 2006.*

Rodriguez et al., "Mapping of copper/hydrogen peroxide-induced DNA damage at nucleotide resolution in human genomic DNA by ligation-mediated polymerase chain reaction," J Biol Chem 270(29):17633-17640, 1995.*

Bastarache, "Black clay safety inquiry," Ceramic Arts Discussion List, Apr. 2002, http://lsv.ceramics.org/scripts/wa.exe?A2=ind0204a& L=clayart& F=&S=&P=33706, printed on Sep. 11, 2006.*

TheCattleSite, "Cow Urine Sale High on Government's Agenda," http://www.thecattlesite.com/news/21552/cow-urine-sale-high-on-governments-agenda, Latest News, Feb. 4, 2008.*

Elkind et al., Actinomycin D inhibition of repair of a DNA complex from Chinese hamster cells, Int. J. Radiat. Biol., 1972, vol. 22, No. 4, pp. 313-324.

"Committee for veterinary medicinal products", The European Agency for the Evaluation of Medicinal Products, Veterinary Medicines Evaluation Unit, Dec. 1997, pp. 1-3.

De Meo, et al., "Genotoxic activity of potassium permanganate in acidic solutions", Mutas Res., Jul. 1991, vol. 260, No. 3, pp. 295-306.

Kessis, et al., "Human papillomavirus 16 E6 expression disrupts the p53-mediated cellular response to DNA damage", Proc. Natl. Acad. Sci. USA, May 1993, vol. 90, pp. 3988-3992.

Hakoda, et al., "Tumor Necrosis Factor-α Plus Actinomycin D-Induced Apoptosis of L929 Cells in Prevented by Nitric Oxide", Surgery Today, Jpn J Surg, 1999, vol. 29, pp. 1059-1067.

* cited by examiner

COMPOSITION (RCUD) FOR PROTECTING AND/OR REPAIRING DNA FROM OXIDATIVE DAMAGES AND A METHOD THEREOF

FIELD OF THE PRESENT INVENTION

A composition useful for protecting and/or repairing DNA from oxidative damages said composition comprising redistilled cow's urine distillate (RCUD) having components benzoic acid, and hexanoic acid, with ammonia content of the composition ranging between 5-15 mg/L, and optionally along with anti-oxidants; and a method of protecting and/or repairing DNA from oxidative damages using composition of claim 1, said method comprising steps of estimating the amount of folded DNA in a sample, mixing the said composition to the said DNA either before or after the exposure of the DNA to the oxidatively DNA-damaging agent, and determining percentage folded DNA in the mixture showing protection and/or repair of DNA from oxidative damages.

BACKGROUND AND PRIOR ART OF THE PRESENT INVENTION

In Veda, the products of cow have been compared with the nectar (Rig-Veda 10.15 pp. 47). In Ayurveda cow's urine is one of the ingredient of Panchagavya. According to Susrut, Cow's urine has several medicinal properties (45/221, pp-61, 72, 220, 221). Its properties are also described by Charak (Solka-100 pp. 72). Cow's urine is extensively used in Ayurveda for purifying certain materials which otherwise possess toxic properties (pp-73).

However, the literature and scripture does not mention urine or its distillate as a protector of cells from DNA damage and chromosomal aberration. To investigate the property of cow urine distillate, the applicants obtained Kamdhenu Ark which is cow urine distillate prepared and marketed by the Govigyan Anusandhan Kendra (GVAK), Nagpur (India). This is the urine distillate suggested for oral ingestion to improve the general health and to control weight gain, oedema, stomach ache, indigestion, skin disease, cardiac problem etc. It is stated in the production process of Kamdhenu Ark that the cow's urine should be fresh as well as free of ammonia. Experiments carried out in NEERI revealed that storage of cow's urine results in formation of ammonia as could be seen from the following Table 1.

TABLE 1

Ammonia concentration in cows urine

| In Open container | | | In Closed container | |
| --- | --- | --- | --- | --- |
| pH | Concentration of ammonia (mg/L) | Time (in Hrs) | Concentration of ammonia (mg/L) | pH |
| 8.0 | 100 | 0 | 100 | 8.0 |
| 8.2 | 953 | 1 | 975 | 8.2 |
| 8.3 | 1055 | 2 | 1232 | 8.4 |
| 8.4 | 1421 | 3 | 1379 | 8.4 |
| 8.5 | 1649 | 4 | 1423 | 8.4 |
| 8.5 | 1849 | 5 | 1710 | 8.5 |
| 8.5 | 1799 | 6 | 1686 | 8.5 |
| 8.5 | 1885 | 7 | 1989 | 8.6 |
| 8.4 | 1600 | 8 | 1850 | 8.6 |
| 8.3 | 1398 | 9 | 1363 | 8.3 |
| 8.5 | 1664 | 10 | 1408 | 8.4 |
| 8.4 | 1441 | 11 | 1033 | 8.3 |
| 8.5 | 1662 | 12 | 1730 | 8.5 |
| 8.3 | 1296 | 13 | 1473 | 8.4 |
| 8.4 | 1535 | 14 | 1511 | 8.4 |
| 8.3 | 1159 | 15 | 1328 | 8.4 |
| 8.6 | 1867 | 16 | 1738 | 8.5 |
| 8.5 | 1662 | 17 | 1862 | 8.7 |
| 8.9 | 2158 | 18 | 1847 | 8.7 |
| 8.9 | 1957 | 19 | 1886 | 8.6 |

The previous work of the applicants was on oxidative damage of the cigarette smoke can be prevented by vitamin C. The Authors demonstrated that the exposure of sub clinical or marginal vitamin C—deficient guinea pigs to cigarette smoke causes oxidation of plasma proteins as well as extensive oxidation degradation of the lung microsomal proteins. Further, cigarette exposure also induces Peroxidation of microsomal lipids as evidenced by the formation of conjugated dienes, malondialdehyde, and fluorescent pigment. However, complete protection against protein damage and lipid Peroxidation occurs when the guinea pigs are fed vitamins. Also, cigarette induced damage of proteins and lipid is reversed after discontinuation of cigarette smoke exposure accompanied by ascorbate therapy. The results if extrapolated to humans, indicate that comparatively large doses of vitamin C may protect the smokers from cigarette smoke-induced oxidative damage and associated degenerative diseases. (Panda, chattopadhyay, and Chatterjee; free radical biology & medicine, Vol. 29, No. 2, pp. 115-124, 2000.)

OBJECTS OF THE PRESENT INVENTION

The main object of the present invention is to develop a natural composition for preventing and rectifying DNA damage.

Another main object of the present invention is to develop a method of preventing and rectifying DNA damage.

Yet another object of the present invention is to develop a process of preparing RCUD. The main objective is to provide new uses of Kamdhenu Ark as a protector of DNA damage.

Another objective of the invention is to provide method for removing ammonia from Kamdhenu Ark with a view to remove toxicity from ammonia, if any, and to improve its activity towards protection of DNA damage.

Still another objective of invention is to identify the active ingredients of the redistilled Kamdhenu Ark which functions as a DNA damage protectant.

SUMMARY OF THE PRESENT INVENTION

A composition useful for protecting and/or repairing DNA from oxidative damages said composition comprising redistilled cow's urine distillate (RCUD) having components benzoic acid, and hexanoic acid, with ammonia content of the composition ranging between 5-15 mg/L, and optionally along with anti-oxidants; and a method of protecting and/or repairing DNA from oxidative damages using composition of claim 1, said method comprising steps of estimating the amount of folded DNA in a sample, mixing the said composition to the said DNA either before or after the exposure of the DNA to the oxidatively DNA-damaging agent, and determining percentage folded DNA in the mixture showing protection and/or repair of DNA from oxidative damages.

DETAILED DESCRIPTION OF THE PRESENT INVENTION

A composition useful for protecting and/or repairing DNA from oxidative damages said composition comprising redistilled cow's urine distillate (RCUD) having components benzoic acid, and hexanoic acid, with ammonia content of the composition ranging between 5-15 mg/L, and optionally along with anti-oxidants; and a method of protecting and/or repairing DNA from oxidative damages using composition of claim 1, said method comprising steps of estimating the amount of folded DNA in a sample, mixing the said composition to the said DNA either before or after the exposure of the DNA to the oxidatively DNA-damaging agent, and determining percentage folded DNA in the mixture showing protection and/or repair of DNA from oxidative damages.

In an embodiment of the present invention, wherein a composition useful for protecting and/or repairing DNA from oxidative damages said composition comprising redistilled cow's urine distillate (RCUD) having components benzoic acid, and hexanoic acid, with ammonia content of the composition ranging between 5-15 mg/L, and optionally along with anti-oxidants.

In another embodiment of the present invention, wherein the RCUD is colorless.

In yet another embodiment of the present invention, wherein the RCUD is water-soluble.

In still another embodiment of the present invention, wherein the RCUD shows specific gravity of about 1.006.

In still another embodiment of the present invention, wherein the RCUD shows pH of range 3.0 to 5.0.

In still another embodiment of the present invention, wherein the RCUD shows ammonical nitrogen ($NH_3N$) of concentration ranging between 5-15 mg/l.

In still another embodiment of the present invention, wherein the RCUD contains volatile fatty acids in the range of 1000 to 3000 mg/l.

In still another embodiment of the present invention, wherein the antioxidants are selected from a group comprising volatile acids, quinoline, and hydrocarbon derivatives.

In still another embodiment of the present invention, wherein volatile fatty acids are derivatives of acetic acid, propionic acid, and butyric acid.

In still another embodiment of the present invention, wherein the derivatives of the volatile acids are Acetic acid-2-propenyl ester; Acetic acid mercapto methyl ester; 2-Butenedinitrile, Fumanonitrile; Propionic acid, 2,2,3-trichloro; Propionic acid-3-chloro; 2-Pentenoic acid-3 methyl; Iso valeric acid; Butanoic acid, 3 hydroxy, ethyl ether; Benzoic acid, 4-methyl 2-trimethyl; Acetic acid[o-(triethyl siloxy) phenyl tri ethyl silyl]; Propionic acid, 3 phenyl (cinnamic acid); Acetic acid mercapto; 1-H indole-3-ol-acetate; Acetic acid phenyl ester; and quinoline, 3-methyl.

In still another embodiment of the present invention, wherein quinoline is selected from a group comprising quinoline 3-methylthi and quinolines 3-methyl.

In still another embodiment of the present invention, wherein the composition smells like urine.

In still another embodiment of the present invention, wherein the composition is used as medicinal composition.

In still another embodiment of the present invention, wherein the said composition is used for analysis for genetic material.

In still another embodiment of the present invention, wherein a method of protecting and/or repairing DNA from oxidative damages using composition of claim 1, said method comprising steps of;

estimating the amount of folded DNA in a sample, mixing the said composition to the said DNA either before or after the exposure of the DNA to the oxidatively DNA-damaging agent, and determining percentage folded DNA in the mixture showing protection and/or repair of DNA from oxidative damages.

In still another embodiment of the present invention, wherein DNA is damaged with compounds selected from a group comprising Actinomycin D, Manganese Oxide ($MnO_2$), and Hydrogen Peroxide ($H_2H_2$).

In still another embodiment of the present invention, wherein said composition enhances anti-genotoxic effect by about 150-250 folds.

In still another embodiment of the present invention, wherein a method of removing ammonia from cow urine distillate to obtain redistilled cow's urine distillate (RCUD), said method comprising steps of re-distillating the cow's urine distillate using Orthophosphoric acid of concentration ranging between 82% to 88%, and obtaining redistilled cow's urine distillate (RCUD).

In still another embodiment of the present invention, wherein a method as claimed in claim 1, wherein the treatment with Orthophosphoric acid brings down the pH level of the distillate to less than 2.

In still another embodiment of the present invention, wherein a method as claimed in claim 1, wherein re-distillating the distillate at temperature of about 100° C.

In still another embodiment of the present invention, wherein a method as claimed in claim 1, wherein the re-distillation helps remove toxicity from cow urine.

In still another embodiment of the present invention, wherein a method as claimed in claim 1, wherein the said method brings down the level of ammonia in the distillate from concentration ranging between 1000-1500 mg/L to concentration ranging between 5-15 mg/L.

A pharmaceutical composition comprising antioxidants containing cow urine distillate in an amount effective to protect DNA damage is disclosed. The antioxidants can be volatile fatty acid.

The invention related to a noble use of redistilled low ammonia containing cow's urine distillate for DNA damage protection. DNA, one of the most critical cellular targets for hazardous chemicals and wastes, may get damaged following exposure by alteration of bases of disruption of sugar phosphate backbone.

When DNA damage occur in cells, the genes responsible for genomic integrity and DNA damage repair mechanism get induced as a result of which cell cycle gets arrested at G1 stage. Thereafter, the damaged DNA is repaired following which the arrested cell cycle resumes and the cell progresses into S-phase (DNA synthesis). However, if the damage could not be repaired then the same gene, which normally carries out the repair, induce the cell to go for apoptosis (programmed cell death) thereby maintaining the system free from defective cells. The present invention has direct implication in facilitating the damage repair caused by DNA damaging chemical such as hydrogen peroxide ($H_2O_2$), actinomycin-D and manganese-dioxide ($MnO_2$).

The ammonia originates from urea present in cow's urine following enzymatic hydrolysis by the enzyme urease present in number of microorganisms. Though ammonia is toxic to human health, the dose at which Kamdhenu Ark is consumed (5 ml at a time) is not likely to exert any adverse health effect or healthy individuals.

However, its removal from the Ark is desirable before human consumption at least for the sensitive population. Therefore Kamdhenu Ark procured from GVAK, Nagpur was treated with orthophosphoric acid following which distillation was again carried out. The redistillation process require addition of 10-25 ml of (85%) Orthophosphoric acid (AR grade) to 400 ml of K-Ark to bring the pH to less than 2 which will immobilize ammonia in the residue. The redistillation was performed at around 100° C. and the distillate was tested for ammonia. It was observed that the ammonia level in the distillate varied between 5-15 mg/l. The removal of ammonia resulted in disappearance of the manifestation of cytotoxicity, which was observed with ammonia containing K-Ark prior to redistillation. The redistilled Kamdhenu-Ark (RCUD) with an ammonia level varying between 5 and 15 mg/l was used for subsequent experiments. The present invention was the result of planned experiment which demonstrated the property of Kamdhenu-Ark as the protector of DNA damage to cells exposed to DNA damaging chemicals.

Cow's urine, one of the components of Panchagavya, is considered to cause weight loss reversal of certain cardiac problems, indigestion, stomach ache, oedema, etc. However, its role in preventing DNA damage has not been mentioned anywhere in the literature and scriptures. Therefore the applicant considered worthwhile to determine the efficiency of redistilled Kamdhenu Ark to protect DNA damage in cells exposed to DNA damaging chemicals in vitro. The applicants also analyzed the redistilled Kamdhenu Ark using gas chromotography-mass spectrography (GC-MS) and identified the components which are likely to act as anti-oxidants to behave like other known antioxidants which are known to protect DNA damage.

The invention relates new uses of cow's urine distillate as a protectant of cellular DNA damaging chemicals such as actinomycin-D, hydrogen peroxide and manganese dioxide. The compounds identified in redistilled cow's urine acts as antioxidants which are known to protect cells from DNA damage.

BRIEF DESCRIPTION OF THE ACCOMPANYING DRAWING

FIG. 1 represents the detector response of GCMS following injection of redistilled Kamdhenu Ark.

This invention is the result of a search of antioxidants of natural origin with a property to protect DNA damage in cells exposed to DNA damaging chemicals. In this endeavour, Kamdhenu Ark was prepared by distilling the urine of specially raised cows on diets containing special herbs as indicated in ancienk scriptures and literature. These cows were raised at GVAK, Deolapar (Nagpur District) under the strict supervision of the inventors from GVAK, Nagpur. The distillate so obtained (around 400 ml/batch), was redistilled by reducing the pH of the distilled Ark to less than 2 by the addition of 10-25 ml of (25%) orthophosphoric acid (AR grade). The redistilled and modified Ark was used for all the experiments conducted subsequently NEERI.

EXAMPLES

In the next step, protection of DNA damaging action caused by actinomycin-D, $H_2O_2$, $MnO_2$ by Kamdhenu Ark was demonstrated. In this endeavor, the applicants experimented with the DNA damaging activities of Actinomycin-D, $H_2O_2$ and $MnO_2$ against the polymorphonuclear leucocytes and protection provided by the test component modified Kamdhenu Ark (redistilled cow's urine distillate) following the method described above. These experiments are being described in the following examples.

When the polymorphonuclear leucocytes were treated a-priori with redistilled cow's urine distillate as well as at the time of adding the DNA damaging chemicals, protection to DNA damage was observed.

In fact, redistilled cow's urine distillate also had a statistically significant ameliorating effect on the DNA damage caused by the above mentioned DNA damaging agents.

The below stated examples are mere elaboration of the invention of the instant Application and should not be construed to limit the scope of the present invention Example-I Elaborates the redistilled cow's urine distillate mediated protection from the DNA damaging chemical actinomycin-D against polymorphonuclear leucocytes (Table-2).

TABLE 2

DNA damage induced by actinomycin D and protection by redistilled cow's urine distillate (modified K-Ark).

| Experimental Details | sets in percentage | | | | | | | |
|---|---|---|---|---|---|---|---|---|
| | Set I | Set II | Set III | Set IV | Set V | Mean | SD | P-Value |
| Control (0.1% DMSO) | 70 | 75 | 69 | 66 | 69 | 70 | 2.92 | — |
| Kamdhenu Ark (Modified) | 70 | 70 | 68 | 74 | 72 | 71 | 2.28 | NS |
| Actinomycin D (Positive control) | 40 | 38 | 44 | 28 | 39 | 38 | 5.30 | *P < 0.001 |

TABLE 2-continued

DNA damage induced by actinomycin D and protection by redistilled cow's urine distillate (modified K-Ark).

| Experimental Details | Set I | Set II | Set III | Set IV | Set V | Mean | SD | P-Value |
|---|---|---|---|---|---|---|---|---|
| Kamdhenu Ark (60 µl) + Actinomicyne-D (pretreatment) | 43 | 43 | 53 | 57 | 26 | 44 | 10.73 | *P < 0.01 |
| Kamdhenu Ark (60 µl) + actinomycine-D simultaneous treatment | 73 | 73 | 77 | 85 | 73 | 76 | 4.66 | NS |

The results are average of five sets of experiments.
*P value calculated in comparison to negative control (0.1% DMSO).
K-Ark dosage tested was 60 µl,
NS = Not significant.

The DNA damage caused by the well known DNA damaging chemical actinomycin-D was statistically significant; P value<0.001.

When cow's urine distillate unmodified Kamdhenu Ark at a volume of 30 µl was simultaneously added with actinomycin D, there was a slight ameliorating effect though the DNA damage observed was statistically significant when compared to control. On the other hand redistilled cow's urine distillate at 30 µl and 60 µl volumes had ameliorating effect on DNA damage when added simultaneously with actinomycin D. The observed anomaly could be attributed to the ammonia content of the unmodified Kamdhenu Ark.

Pretreatment of polymorphonuclear leucocytes (PMNs) with 60 µl of redistilled cow's urine distillate, prior to exposure to Actinomycin-D, did not result in significant DNA damage showing that redistilled cow urine distillate can protect cells from DNA damage.

Post treatment of PMNs with redistilled cow urine distillate 10 min after exposure to actinomycin-D did not result in statistically significant DNA damage.

Example-2

Elaborates the redistilled cow's urine distillate mediated protection from the DNA damaging chemical hydrogen peroxide ($H_2O_2$) against polymorphonuclear leucocytes (Table-3).

TABLE 3

DNA damage induced by hydrogen peroxide ($H_2O_2$) and protection by redistilled cow's urine distillate.

| Experimental Details | Set I | Set II | Set III | Set IV | Set V | Mean | SD | P-Value |
|---|---|---|---|---|---|---|---|---|
| Control(0.1% DMSO) | 80 | 71 | 70 | 71 | 87 | 76 | 2.92 | — |
| Kamdhenu Ark (modified) | 70 | 70 | 68 | 74 | 72 | 71 | 2.28 | NS |
| Hydrogen Peroxide ($H_2O_2$) (Positive control) | 20 | 29 | 24 | 43 | 38 | 31 | 8.56 | *P < 0.001 |

TABLE 3-continued

DNA damage induced by hydrogen peroxide ($H_2O_2$) and protection by redistilled cow's urine distillate.

| Experimental Details | Set I | Set II | Set III | Set IV | Set V | Mean | SD | P-Value |
|---|---|---|---|---|---|---|---|---|
| $H_2O_2$ + Kamdhenu Ark pretreatment | 43 | 43 | 53 | 57 | 26 | 44 | 10.73 | *P < 0.01 |
| $H_2O_2$ + Kamdhenu Ark simultaneous treatment) | 69 | 67 | 85 | 71 | 60 | 70 | 8.18 | *P > 0.05 |
| $H_2O_2$ + Kamdhenu Ark post treatment | 60 | 61 | 75 | 61 | 62 | 64 | 5.64 | *P > 0.05 |

The results are average of five sets of experiments.
*P value calculated in comparison to negative control (0.1% DMSO),
K-Ark dosage tested was 60 µl,
NS = Not significant The DNA damage caused by the well known DNA damaging chemical hydrogen peroxide was statistically significant; (P<0.001).

Pretreatment of polymorphonuclear leucocytes (PMNs) with 60 µl of redistilled cow's urine distillate, did not result in statistically significant DNA damage in cells exposed to $H_2O_2$ and redistilled cow's showing that redistilled cow urine distillate can protect cells from DNA damage.

The same results were obtained when $H_2O_2$ and redistilled cow's urine distillate were added simultaneous post treatment of PMNs with redistilled cow urine distillate 10 minute after exposure to hydrogen peroxide also did not result in statistically significant DNA damage.

Example-3

Elaborates the redistilled cow's urine distillate mediated protection from the DNA damaging chemical manganese dioxide ($MnO_2$) against polymorphonuclear leucocytes (Table-4).

TABLE 4

DNA damage induced by manganese dioxide ($MnO_2$) and protection by redistilled cow's urine distillate.

(sets in percentage)

| Experimental Details | Set I | Set II | Set III | Set IV | Set V | Mean | SD | P-Value |
|---|---|---|---|---|---|---|---|---|
| Control(0.1% DMSO) | 80 | 71 | 70 | 71 | 87 | 76 | 6.68 | — |
| Kamdhenu Ark (modified) | 70 | 70 | 68 | 74 | 72 | 71 | 2.28 | NS |
| Manganese dioxide ($MnO_2$) 20 μl (Positive control) | 22 | 30 | 22 | 15 | 16 | 21 | 5.36 | *P < 0.001 |
| Manganese dioxide ($MnO_2$) 20 μl + Kamdhanu Ark modified 60 μl simultaneous treatment) | 60 | 67 | 60 | 60 | 60 | 61 | 2.80 | NS |

The results are average of five sets of experiments.
*P value calculated in comparison to negative control (0.1% DMSO).
K-Ark dosage tested was 60 μl,
NS = Not significant.

The DNA damage caused by the well known DNA damaging chemical manganese dioxide was statistically significant (P<0.001). Polymorphonuclear leucocytes (PMNs) were exposed simultaneously to $MnO_2$ and 60 μl of redistilled cow urine distillate, no statistically significant DNA damage was observed.

Example-4

Elaborates the redistilled cow's urine distillate (1 μl concentration) mediated protection from the DNA damaging chemical hydrogen peroxide ($H_2O_2$) against polymorphonuclear leucocytes (Table-5).

TABLE 5

DNA damage induced by hydrogen peroxide ($H_2O_2$) and protection by redistilled cow's urine distillate (1 μl concentration).

Sets in percentage

| Experimental Details | Set I | Set II | Set III | Set IV | Set V | Mean | SD | P-Value |
|---|---|---|---|---|---|---|---|---|
| Control(0.1% DMSO) | 70 | 70 | 69 | 66 | 69 | 70 | 2.92 | — |
| Kamdhenu Ark Modified (1 μl) | 62 | 59 | 60 | 66 | 62 | 62 | 2.68 | NS |
| $H_2O_2$ (Positive control) 10 μl | 24 | 24 | 24 | 33 | 24 | 26 | 4.02 | *P < 0.001 |
| $H_2O_2$ (10 μl) + Kamdhenu Ark Modified (1 μl) | 67 | 68 | 66 | 68 | 68 | 67 | 0.89 | NS |

The results are average of five sets of experiments.
*P value calculated in comparison to negative control (0.1% DMSO).
K-Ark dosage tested was 1 μl,
NS = Not significant.

The DNA damage caused by the well known DNA damaging chemical hydrogen peroxide was statistically significant (P<0.001).

Simultaneous treatment of polymorphonuclear leucocytes (PMNs) with 1 μl of redistilled cow's urine distillate to hydrogen peroxide did not result in statistically significant DNA damage showing that redistilled cow urine distillate can protect cells from DNA damage even when added at a level of 1 μl.

Example-5

Elaborates the Comparison of protective action of Cow urine distillate (1 μl concentration) and redistilled cow urine distillate (1 μl concentration) on DNA strand break induced by hydrogen peroxide ($H_2O_2$) against polymorphonuclear leucocytes (Table-6).

TABLE 6

Comparison of protective action of Cow urine distillate (1 μl concentration) and redistilled cow urine distillate (1 μl concentration) on DNA strand break induced by hydrogen peroxide ($H_2O_2$).

sets in percentage

| Experimental Details | Set I | Set II | Set III | Set IV | Set V | Mean | SD | P-Value |
|---|---|---|---|---|---|---|---|---|
| Control(0.1% DMSO) | 70 | 75 | 69 | 66 | 69 | 70 | 2.92 | — |
| Kamdhenu Ark Modified (1 μl) | 62 | 66 | 60 | 66 | 62 | 63 | 2.68 | N.S. |
| Kamdhenu Ark (with ammonia) 1 μl | 46 | 37 | 45 | 34 | 45 | 41 | 5.50 | *P < 0.001 |
| $H_2O_2$ (Positive control) 10 μl | 24 | 24 | 24 | 33 | 24 | 26 | 4.02 | *P < 0.001 |
| $H_2O_2$ (10 μl) + Kamdhenu Ark Modified (1 μl) | 67 | 68 | 66 | 68 | 68 | 67 | 0.89 | N.S. |
| $H_2O_2$ (10 μl) + Kamdhenu Ark (with ammonia) 1 μl | 42 | 32 | 33 | 34 | 33 | 35 | 4.08 | *P < 0.001 |

The results are average of five sets of experiments.
*P value calculated in comparison to negative control (0.1% DMSO).
K-Ark dosage tested was 1 μl,
NS = Not significant.

The DNA damage caused by the well known DNA damaging chemical hydrogen peroxide was statistically significant (P<0.001).

Simultaneous treatment of polymorphonuclear leucocytes (PMNs) with 1 μl of cow urine distillate to hydrogen peroxide showed statistically significant DNA damage. However, the redistilled cow urine distillate could protect cells from DNA damage. This invention is the result of a search for antioxidants of natural origin with a property to protect DNA damage in cells exposed to DNA damaging chemicals.

In an embodiment of the present invention, of redistilled cow's urine distillate was experimented as a positive agent from DNA damaging chemicals.

In an embodiment, the redistilled cow's urine distillate was found to contain antioxidants such as 1) benzoic acid, hexanoic acid. In still another embodiment the redistilled cow's urine distillate was used as a positive agent for DNA damage caused by actinomycin D.

In an embodiment, the redistilled cow's urine distillate was found to contain antioxidant such as 1) benzoic acid, hexanoic acid. In still another embodiment, the redistilled cow's urine distillate was used as a protection agent for DNA damage caused by $H_2O_2$.

In an embodiment, the redistilled cow's urine distillate was found to contain antioxidant. In still another embodiment the redistilled cow's urine distillate was used as a positive agent for DNA damage caused by $MnO_2$ In yet another embodiment, the effect of redistilled cow's urine distillate as a protective agent for DNA damaging chemical was studied after pre, simultaneous and post treatment of PMN's prior to exposure to DNA damaging chemicals.

In still another embodiment the cow's urine distillate shown as having DNA damaging property which was mitigated by redistillation whereby ammonia present in the cow's urine distillate was removed from a range of 1000-1500 mg/l to a range of 5-15 mg/l.

In yet another the Redistilled Cow Urine Distillate (RCUD) at a volume of 60 µl could result in providing protection to PMN's following exposure to actinomycin D.

In still another embodiment the Redistilled Cow Urine Distillate at a volume of 60 µl could result in providing protection to PMN's following exposure to $MnO_2$.

In yet another embodiment the Redistilled Cow Urine Distillate at a volume of 60 µl could result in providing protection to PMN's following exposure to $H_2O_2$.

In still another embodiment the Redistilled Cow Urine Distillate at a volume of 1 µl could result in providing protection to PMN's following exposure to $H_2O_2$.

| Preparation of reagents | |
|---|---|
| Solution A | |
| 0.56% Ammonium chloride<br>10 mM Tris<br>Balanced salt solution (BSS) | pH 7.2 |
| 137 mM Nacl<br>5 mM Kcl<br>8.5 mM $Na_2HPO_4$, 8.5 mM $NaH_2PO_4$<br>10 mM Hepes<br>0.8 mM $MgSO_4$<br>5 mM Glucose<br>Solution B | pH 7.4 |
| 0.25 M Inositol<br>10 mM $NaH_2PO_4$ - 10 mM $Na_2HPO_4$<br>Solution C | pH 7.2 |
| 9 M-Urea<br>10 mM - NaOH<br>2.5 mM - EDTA<br>0.1% sodium dodysil sulfate<br>Solution D | |
| 0.2 N - NaOH<br>Solution E | |
| 1 M - glucose<br>100 µl - Mercaptoethanol<br>Solution F | |
| 6.7 µg/ml Ethidium bromide<br>Actinomycin-D 1 µg/ml of 0.1%<br>DMSO (Dimethyl Sulphoxide)<br>$H_2O_2$ | |
| 150 µM<br>$MnO_2$ | |
| 250 ppm or 250 mg/l (stock) | |

Assay for DNA Damage and its Protection by RCUD

To 5 ml of whole blood 15 ml of solution A is added, mixed well and kept between 2 and 4° C. for 30 minutes. The mixture was centrifuged at 800×g for 10 minutes. The supernatant is discarded, the pellet was washed with balanced salt solution and washing is discarded after centrifugation at 800×g for 10 minutes. This step was done twice. The pellet comprises of peripheral polymorphonuclear leukocytes (PMNs) which are suspended in predetermined amount of solution B.

One ml of PMNs suspended in solution B containing around 1×10⁶ cells are separately treated with 10 µl of actinomycin D, 10 µl of $H_2O_2$ and 2.5-20 mg/l (in final volume) of MnO2; one more tube was kept as control where 0.1% DMSO (negative control) was added. The volume in each tube was made up to 2 ml by adding BSS solution. The mixture is incubated at 37° C. for 1 hr in 5% $CO_2$ incubator with 95% humidity. After incubation, 5 ml of ice cold 0.9% NaCl was added in each tube, centrifuged at 800 g for 10 minutes and the supernatant is discarded. To the pellet in each tube 1.5 ml of solution B was added. The tubes (control and three experimental) are mixed thoroughly and the mixture was equally distributed in the volume of 0.2 ml in 3 tubes designated as B, P and T, then 200 µl of solution C was added. The three tubes B, P & T, were kept in cold (0° C.) for 10 minutes after mixing well in order to lyse the cells. To tube T 400 µl of solution E was added. Thereafter, 200 µl of solution D was added to all the tubes B, P and T. The tubes were kept at 0° C. for 30 minutes. Thereafter, contents of the B tube was sonicated for 30 second three times. B, P and T were further incubated at 20° C. for 1 hr. To B and P tubes 400 µl of solution E was added and the tubes were incubated at 0° C. for 10 minutes. 1.5 ml of solution F are added to all the tubes, homogenized on a vortex shaker and subjected to fluorescence spectrophotometric analyses within 15 minutes with 520 nm excitation and at 590 nm emission. The percentage of double stranded DNA remaining was determined using the following formula. [Krishnamurthi et al. (2003) & Bimboim & Jevcak (1981)].

$$\% \text{ of double stranded DNA} = \frac{P - B}{T - B} \times 100$$

Where P, B and T are the fluorescence emissions at 590 nm.

One ml of PMNs suspended in solution B containing around 1×10⁶ cells were taken in four tubes A, B, C and D. To tube B, 60 µl of redistilled cow urine distillate (RCUD) was added and incubated at 37° C. for 10 minutes.

To tube C was added the DNA damaging chemical (Actinomycin-D or $H_2O_2$ or $MnO_2$), incubated at 37° C. for 10 minutes and thereafter, 60 µl of RCUD was added. To tube A only 60 µl of RCUD was added; the volume was made up with BSS. The mixture was incubated at 37° C. for 1 hr in 5% $CO_2$ incubator with 95% humidity. The rest of the protocol was followed as described under C and D.

REFERENCES

1. Krishnamurthi, K.; Saravana Devi, S.; Chakrabarti, T. Genotoxic effects of PAH containing sludge extracts in Chinese hamster ovary cell cultures. Biomedical and Environmental Sciences 2003, 16 (1), 76-89.
2. Bimboim H. C and J. J. Jevcak (1981) Fluorometric Method for Rapid Detection of DNA strand breaks in Human white blood cells produced by low Doses of Radiation, *Cancer Res.*, 41: 1889-1892.

The invention claimed is:

1. An in vitro method of inhibiting oxidative damage to DNA of human polymorphonuclear cells from oxidative damage comprising:

exposing human polymorphonuclear cells to a composition comprising approximately 60 µl/ml of redistilled cow's urine distillate (RCUD), wherein RCUD comprises benzoic acid; acetic acid-2 propenyl ester; acetic acid mercapto methyl ester; 2-butenedinitrile furanonitrile; propionic acid 2,2,3-trichloro; propionic acid-3-chloro; 2-pentenoic acid-3 methyl; iso valeric acid; butanoic acid, 3 hydroxy, ethyl, ether; benzoic acid, 4 methyl 2 trimethyl; acetic acid phenyl trimethylsilyl; propionic acid; Cinnamic acid; acetic acid mercapto; 1-H indole-3-ol-acetate; acetic acid phenyl ester; and quinoline, 3-methyl;

wherein the composition has ammonia content ranging between 5 and 15 mg/l, wherein said RCUD is exposed to said human polymorphonuclear cells before or at the same time that said cells are exposed to a DNA damaging amount of $H_2O_2$.

2. The method of claim 1, wherein the composition further comprises at least one antioxidant.

3. The method of claim 1, wherein the composition reduces the genotoxic effect caused by the oxidative DNA damaging agent by approximately 150-250 percent.

4. The method of claim 1, wherein the composition is colorless.

5. The method of claim 1, wherein the composition is water-soluble.

6. The method of claim 1, wherein the composition has a specific gravity of about 1.006.

7. The method of claim 1, wherein the composition has a pH ranging between 3.0 and 5.0.

8. The method of claim 1, wherein the composition has an ammonical nitrogen ($NH_3N$) concentration ranging between 5-15 mg/L.

9. The method of claim 1, wherein the composition contains volatile fatty acids in the range of 1000 to 3000 mg/l.

10. The method of claim 1, wherein the composition smells like urine.

\* \* \* \* \*